(12) United States Patent
Murai

(10) Patent No.: US 8,871,944 B2
(45) Date of Patent: Oct. 28, 2014

(54) THIAZOLE DERIVATIVE AND PROCESS FOR PRODUCING SAME

(75) Inventor: Toshiaki Murai, Gifu (JP)

(73) Assignee: Gifu University, Yanagido, Gifu-shi, Gifu (JP)

( * ) Notice: Subject to any disclaimer, the term of this patent is extended or adjusted under 35 U.S.C. 154(b) by 118 days.

(21) Appl. No.: 13/255,202

(22) PCT Filed: Mar. 8, 2010

(86) PCT No.: PCT/JP2010/053765
§ 371 (c)(1),
(2), (4) Date: Sep. 7, 2011

(87) PCT Pub. No.: WO2010/104027
PCT Pub. Date: Sep. 16, 2010

(65) Prior Publication Data
US 2011/0319616 A1    Dec. 29, 2011

(30) Foreign Application Priority Data

Mar. 10, 2009  (JP) ............................. JP2009-055787

(51) Int. Cl.
*C07D 277/42* (2006.01)
*C07D 417/04* (2006.01)
*C07D 277/18* (2006.01)
*C07D 417/14* (2006.01)

(52) U.S. Cl.
CPC ............ *C07D 277/18* (2013.01); *C07D 277/42* (2013.01); *C07D 417/04* (2013.01); *C07D 417/14* (2013.01)
USPC ......... 548/190; 548/193; 544/135; 546/270.4

(58) Field of Classification Search
USPC ........ 544/135; 546/256, 270.4; 548/190, 194, 548/193
See application file for complete search history.

(56) References Cited

U.S. PATENT DOCUMENTS 5,104,889 A    4/1992  Kanai et al.

FOREIGN PATENT DOCUMENTS

| CN | 101265257 A | 9/2008 |
|---|---|---|
| JP | 05194506 A | 8/1993 |
| JP | 06048907 A | 2/1994 |
| JP | 06145169 A | 5/1994 |
| JP | 01087490 A | 4/1998 |
| JP | 11-222483 A | 8/1999 |
| JP | 11209284 A | 8/1999 |
| JP | 11269174 A | 10/1999 |
| JP | 2002053566 A | 2/2002 |
| JP | 2006225334 A | 8/2006 |
| WO | 02/094798 A1 | 11/2002 |
| WO | 2004014884 A1 | 1/2006 |

OTHER PUBLICATIONS

Dorwald, Side Reactions in Organic Synthesis, 2005, Wiley: VCH Weinheim Preface, pp. 1-15 & Chapter 8, pp. 279-308.*
Mercey et al. "Efficient synthesis of primary, etc.," Tetrahedron Letters 49 (2008) 6553-6555.*
Liu, L., Synthesis and biological activity of 2-indolyl oxazoline and thiazoline derivatives, Youji Huaxue, 2008, 28(10), p. 1841-1845 Scheme 1, 2f, 2g.
Abrunhosa, I., Chiral thiazoline ligands: application in Pd-catalysed allylic substitution, Tetrahedron, 2004, 60(41), p. 9263-9272, Compound 5f.
Suzuki, J., Synthesis and Activity of Novel Acaricidal/Insecticidal 2, 4-Diphenyl-1,3-oxazolines, Nippon Noyakugaku Zasshi, 2002, 27(1), p. 1-8, Table 5, Compound No. 119.
McKeon, S. C., New Thiazoline-Oxazoline Ligands and Their Application in the Asymmetric Friesel-Crafts Reaction, European Journal of Organic Chemistry, 2009, (28), p. 4833-4841, Scheme 1, compound 6c.
Murai, Toshiaki, et al., N-Thioacyl 1,3-Amino Alcohols: Synthesis via Ring-Opening of Oxiranes with Thioamide Dianions and Applications as Key Intermediates Leading to Stereochemically Defined 5,6-Dihydro-4H-1,3-oxazines and 1,3-Amino Alcohols, Journal of Organic Chemistry, 2005, v. 70 (20), p. 8148-8153.
Murai, Toshiaki, et al., Silylation and alkylation of thioamide dianions of N-arylmethyl secondary thioamides, and reduction of the resulting thioamides leading to secondary and primary amines, Journal of Sulfur Chemistry, 2009, v. 30 Nos. 3-4, p. 225-235.

\* cited by examiner

*Primary Examiner* — Patricia L Morris
(74) *Attorney, Agent, or Firm* — GFD Patents LLC; Gerald F. Dudding

(57) ABSTRACT

An object is to provide a thiazole derivative produced from easily available raw materials by a simplified production process. Provided are a process for producing a novel thiazole derivative represented by the general formula (I), which is characterized by adding a strong base to a thioamide represented by the general formula (II) and reacting the mixture with a thioformamide represented by the general formula (III), and a novel thiazole derivative.

7 Claims, 1 Drawing Sheet

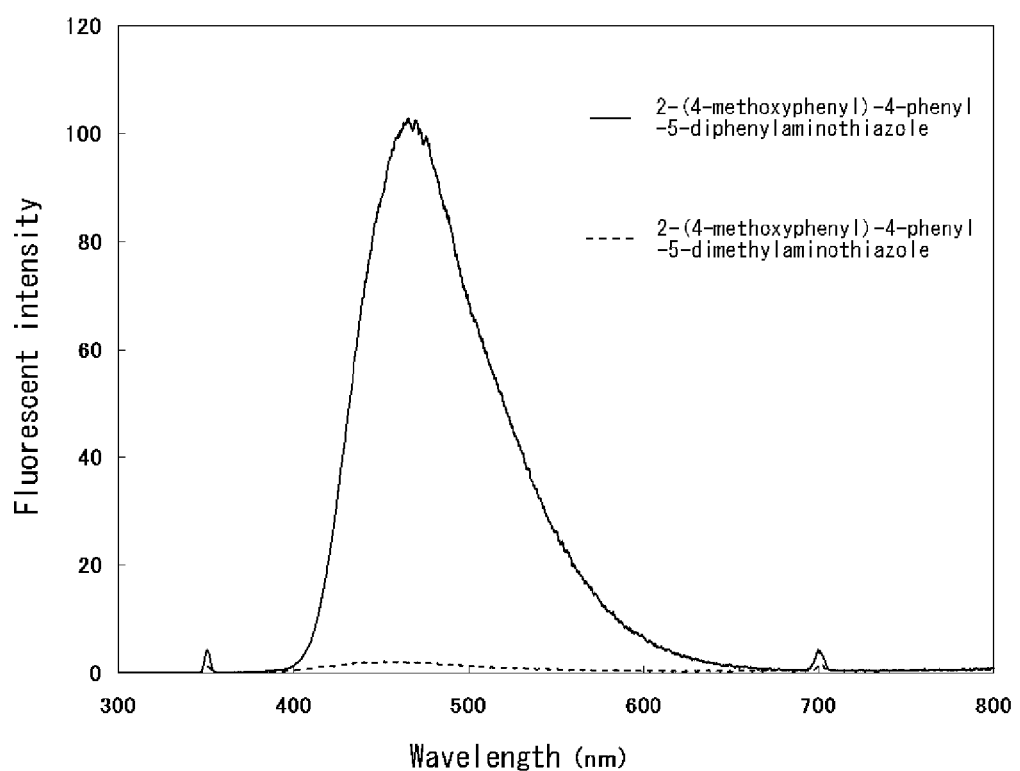

THIAZOLE DERIVATIVE AND PROCESS FOR PRODUCING SAME

TECHNICAL FIELD

The present invention relates a thiazole derivative and a process for producing the same. More specifically, the present invention relates to a process for producing a pyridyl thiazole compound or a dihydrothiazole compound at a high yield, inexpensively, simply and selectively.

BACKGROUND ART

A thiazole derivative is a useful compound as a functional compound (or a synthesis intermediate thereof) such as an agricultural chemical (insecticide, etc.), a medical product, a fungicide and a dye, and an electronic material. Examples thereof include a thiazole derivative that is a compound having a thiazole skeleton used as an interleukin-6 production inhibitor/bone absorption inhibitor/anti-osteoporosis agent (Patent Document 1), a thiazole derivative used as a bone forming accelerator (Patent Document 2), a thiazole derivative used as a protein kinase C inhibitor (Patent Document 3), a thiazole derivative used as an agricultural chemical intermediate (Patent Document 4), and a thiazole derivative used as a neuropeptide Y antagonist (Patent Document 5).

In these documents, various methods are disclosed as synthesis examples of thiazole derivatives. For example, bromine is dropped into a dichloromethane solution of 4'-chloropropiophenone to be acted and the mixture is then reacted with thiourea (Patent Documents 1 and 2), a method of adding 3-chloroacetylacetone to an ethanol solution of thiourea and reacting with heating, and then adding a poor solvent to be deposited by cooling (Patent Document 3), a method of mixing difluorophenacyl bromide and cyanothioacetamide in water to be reacted with heating (Patent Document 4), and a method of mixing β-acetonaphtone and thiourea, and tetrabutylammonium bromide in ethyl acetate and dropping bromine thereinto to be reacted (Patent Document 6). These methods respectively remain rooms for improvements with respect to using bromine that has a pungent odor, with respect to necessity of obtaining particular reagents, and the like.

On the other hand, a pyridyl thiazole compound that is one of thiazole derivatives is useful as a fungicidal composition, and a production process thereof is described in the following document (Patent Document 7). According to the document, 2,6-dibromopyridine is treated with alkyl lithium and N,N-dimethyl acetoamide is then added thereto. The reaction mixture is brominated with a brominating agent in the presence of an acid and then reacted with thioacetamide and, finally by a coupling reaction with alkyl halogen, a desired pyridyl thiazole compound is thus obtained. This process includes a step with multiple stages and thus has a problem with respect that an operation method thereof is somewhat complicated.

Furthermore, for a preparation process of dihydrothiazole (referred to as thiazoline in IUPAC, and referred to as dihydrothiazole in order to clarify difference from thiazole in the present invention) that is one of thiazole derivatives, proposed is, for example, a method of mixing methyl 2-(difluoromethyl)-5-(((2-chloroethyl)amino)carbonyl)-4-(2-methylpropyl)-6-trifluoromethyl)-3-pyridinecarboxylate and diphosphorus pentasulfide with heating and degassing to produce dihydrothiazole (Patent Document 8). In this method, a particular starting substance is required in order to obtain a 4,5-dihydrothiazole compound having a pyridyl group at the 2nd position.

PRIOR ART DOCUMENTS

Patent Documents

Patent Document 1: Japanese Unexamined Patent Application Publication (JP-A) No. Hei10-87490
Patent Document 2: JP-A No. Hei11-209284
Patent Document 3: JP-A No. 2002-53566
Patent Document 4: Domestic re-publication of PCT application No. WO2002/094798
Patent Document 5: Japanese Unexamined Patent Application Publication (Translation of PCT Application) No. 2006-502131
Patent Document 6: JP-A No. 2006-225334
Patent Document 7: JP-A No. Hei5-194506
Patent Document 8: JP-A No. Hei11-269174

DISCLOSURE OF INVENTION

Problems to be Solved by the Invention

As described above, a thiazole derivative is very useful as an intermediate of a functional material such as a pharmaceutical composition and a dye, and an electronic material; however, in a conventional synthesis method, there has been considered to have a room for improvements such as particularity of raw materials to be used and necessity of production steps with multiple stages. Therefore, an object in the present invention is to propose a simplified production process using easily available raw materials.

Means for Solving the Problems

As a result of intensive studies made in order to solve the above described problems and achieve the desired object, it was found in the present invention that when a thioamide is synthesized and then acted with a thioformamide through a thioamide dianion, thiazole or dihydrothiazole can be selectively synthesized by a substituent of the thioamide.

That is, the present invention relates to a process for producing a thiazole derivative represented by the general formula (I), wherein a strong base is added to a thioamide represented by the general formula (II) and the mixture is then reacted with a thioformamide represented by the general formula (III):

[Formula 1]

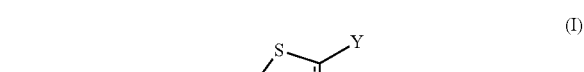

(I)

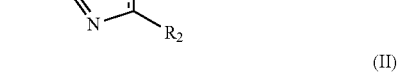

(II)

(III)

wherein -----

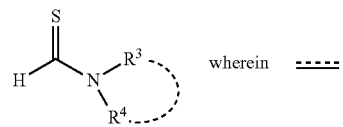

represents a single bond or a double bond, R1 represents a group selected from a branched or cyclic alkyl group having 3 to 12 carbon atoms, an aryl group, and a heteroaromatic group, and each of the groups may be further substituted with one or more substituents selected from halogen, hydroxy, lower alkyl, lower alkoxy, and halo lower alkyl;

$R^2$ represents an aryl group that may be substituted with one or more substituents selected from halogen, hydroxy, lower alkyl, lower alkoxy, and halo lower alkyl, or a pyridyl group that may be substituted with one or more substituents selected from halogen, hydroxy, lower alkyl, lower alkoxy, and halo lower alkyl;

$R^3$ and $R^4$ are the same or different, and each represents a group selected from a linear, branched or cyclic alkyl group having 1 to 12 carbon atoms, an aryl group, and a heteroaromatic group (wherein each of the groups may be further substituted with one or more substituents selected from halogen, hydroxy, lower alkyl, lower alkoxy, and halo lower alkyl), or $R^3$ and $R^4$ represent a $C_5$ to $C_7$ heterocyclic ring formed together with a nitrogen atom to which $R^3$ and $R^4$ are bonded; and Y represents a hydrogen atom or

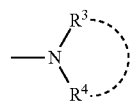

It is characterized in that when $R^2$ is an aryl group, dihydrothiazole represented by the following general formula (IV) is selectively obtained, and when $R^2$ is a pyridyl group, thiazole represented by the following general formula (VI) is selectively obtained:

[Formula 2]

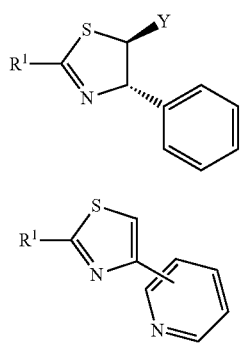

$R^1$ in the above formula is the same as a group represented in the general formula (I) and the general formula (II), and Y is the same as a group represented in the general formula (I).

Such a selective reaction has not been known at all so far, and the reaction mechanism thereof will be specifically described later. A desired thiazole derivative can be synthesized according to this selectivity, which thus makes it possible to obtain broad candidate compounds including applications and functions in the pharmaceutical field and the basic material field by a simple method.

Examples of a strong base added to a thioamide represented by the general formula (II) include n-butyllithium, lithium diisopropylamide, sodium hydride, potassium hydride, potassium t-butoxide, calcium hydride, sodium hydroxide, and sodium amide. These strong bases act on carbon adjacent to the nitrogen atom in the thioamide to extract hydrogen and form a thioamide dianion. n-butyllithium is preferably used as a strong base.

Further, dihydrothiazole as represented by the general formula (IV) is a totally novel compound in which an amino group is bonded to the 5th position in a thiazoline ring. Thiazoline has been known as an intermediate of a medical drug or an agricultural chemical and, in the present invention, an amino group and a phenyl group are respectively bonded instead of a conventional hydrogen atom and the 4th and 5th positions become asymmetric carbons, and thus, a new possibility for an optical activity can also be searched.

In addition, a thioformamide represented by the general formula (III) is reacted and iodine is then added thereto to be reacted, thereby enabling to obtain a thiazole derivative represented by the following general formula (V), other than dihydrothiazole represented by the general formula (IV).

[Formula 3]

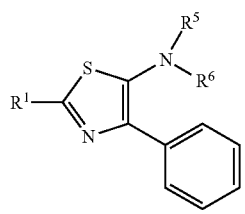

In the formula, $R^1$ is the same as a group shown in the general formula (I). $R^5$ and $R^6$ are the same or different, and each represents a group selected from a linear, branched or cyclic alkyl group having 1 to 12 carbon atoms, an aryl group, and a heteroaromatic group (wherein each of the groups may be further substituted with one or more substituents selected from halogen, hydroxy, lower alkyl, lower alkoxy, and halo lower alkyl), or at least one of $R^5$ and $R^6$ represents an aryl group that may be substituted with one or more substituents selected from halogen, hydroxy, lower alkyl, lower alkoxy, and halo lower alkyl, or a heteroaromatic group that may be substituted with one or more substituents selected from halogen, hydroxy, lower alkyl, lower alkoxy, and halo lower alkyl.

A thiazole derivative represented by the general formula (V) has intensive fluorescence emission particularly when $R^5$ and $R^6$ are aryl groups, that is, the 5th position in a thiazole ring is a diarylamino group, and is a compound that can be expanded to an electron transfer layer, and the like in an organic electroluminescence element (hereinafter electroluminescence is abbreviated as "EL").

Effect of the Invention

The method for producing a thiazole derivative of the present invention can simply and easily produce a thiazole derivative from easily available, inexpensive raw materials without undergoing a complicated synthesis path, which thus can achieve to reduce synthesis cost. Furthermore, for a synthesized product, specifying a substituent of a thioamide makes it possible to obtain a generated product selectively, and also, a totally novel compound that has never existed so far can be easily obtained; therefore, the obtained thiazole derivative can bring significant contribution to creation of a novel compound useful as medical drugs and agricultural chemicals, etc.

Furthermore, addition of iodine to a reaction system enables to obtain a thiazole derivative having extension in a conjugated system, and broad applications for development of new electronic materials can be expected.

BRIEF DESCRIPTION OF DRAWINGS

FIG. 1 is a view showing a fluorescence spectrum for one example of the thiazole derivative of the present invention (Example 6).

MODES FOR CARRYING OUT THE INVENTION

The production process of the present invention will be more specifically described below.

The present invention is characterized by adding a strong base to a thioamide and then reacting the mixture with a thioformamide, and the following reaction formula (a) can be utilized as one example of a synthesis method of the thioamide:

[Formula 4]

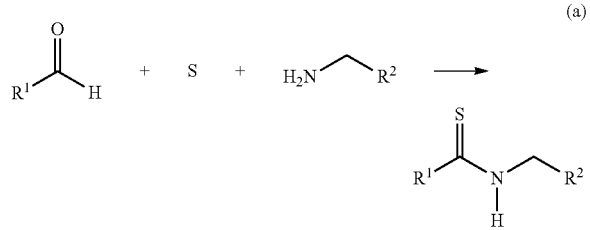

In the formula, $R^1$ represents a group selected from a branched or cyclic alkyl group having 3 to 12 carbon atoms, an aryl group, and a heteroaromatic group, and each of the groups may be further substituted with one or more substituents selected from halogen, hydroxy, lower alkyl, lower alkoxy, and halo lower alkyl. Examples of such a branched alkyl group include isopropyl, isobutyl and t-butyl, examples of a cyclic alkyl group include cyclopropyl and cyclohexyl, examples of an aryl group include benzyl, tolyl and xylyl, and examples of a heteroaromatic group include pyridyl, furyl and thienyl. These groups are preferable because of high yield when a thioamide dianion is formed by a reaction with a strong base.

$R^2$ in the formula represents an aryl group that may be substituted with one or more substituents, or a pyridyl group that may be substituted with one or more substituents. More specifically, $R^2$ represents a group selected from a phenyl group that may be substituted with 1 or 2 groups selected from a halogen atom, a hydroxyl group, an alkyl group having 1 to 6 carbon atoms, an alkoxy group having 1 to 6 carbon atoms, and an alkoxycarbonyl group having 1 to 6 carbon atoms, respectively, or a pyridyl group that may be substituted with 1 or 2 groups selected from a halogen atom, a hydroxyl group, an alkyl group having 1 to 6 carbon atoms, an alkoxy group having 1 to 6 carbon atoms, and an alkoxycarbonyl group having 1 to 6 carbon atoms, respectively, which is a group being a key to selectively synthesizing the thiazole derivative of the present invention.

The above described reaction formula (a) is a method conventionally known as a synthesis method of thioamide that is a starting substance of the present invention. This method is characterized in that any of the raw materials (compounds in the left side of the formula) can be easily and inexpensively obtained, structure design of a thioamide can be freely performed as a result thereof, and the like. However, $R^2$ is used selectively in the present invention for synthesis of a desired thiazole derivative.

In this reaction, dimethylformamide, dimethylsulfoxide, N-methylpyrrolidone, toluene, and the like can be used as an organic solvent. Among these substances, when a thioamide is once purified and then isolated and stored, etc., dimethylformamide is preferable from the viewpoint that a generated product is easily separated in a process of washing a reaction system with water.

In addition, this reaction is performed at 60 to 110° C., and preferably 80 to 90° C. When the reaction is preformed at a lower temperature than the above temperature, a reaction speed is lowered and a yield tends to decrease, and when the reaction is performed at a higher temperature, a side reaction easily occurs and there is a possibility to take trouble in purification.

The above reaction can be performed within the range of molar ratios of an aldehyde group-containing compound: sulfur:amino group-containing compound=1:1:1 to 1:1.2:1.2. The most preferable ratio among these is 1:1.1:1.1, since an aldehyde group-containing compound is completely reacted and purification of a thioamide is effectively promoted. In addition, this reaction is called the Willgerodt-Kindler reaction and described in detail in the document (Brown, E. V. Synthesis 1975, 358).

A synthesis path of dihydrothiazole when a compound having a phenyl group for $R^2$ is used as the above described amino group-containing compound will be shown below:

[Formula 5]

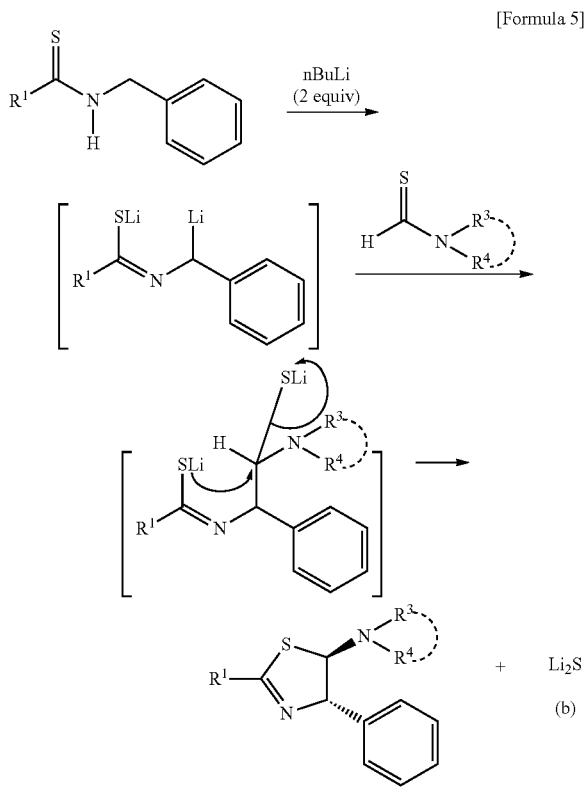

The upper reaction of the above described reactions is to generate a thioamide dianion. Specifically, the reaction is a reaction disclosed in the document (Murai, T. et al., J. Org. Chem. 2005, 70, 8153), etc. A point to remember in initiation of this reaction is necessity to perform the reaction in an inert gas atmosphere such as nitrogen or argon under a dehydrated condition. A thioamide dianion obtained by reacting with a strong base has a possibility for being easily dissolved due to presence of water or oxygen, and is made stably exist to transfer to the next reaction. In addition, lithium diisopropylamide, sodium hydride, potassium hydride, potassium t-butoxide, calcium hydride, sodium hydroxide, sodium amide, and the like can also be used as other strong bases, and butyllithium (nBuLi) is preferable from the viewpoints of reactivity, price, and availability. Furthermore, use of butyllithium leads to an advantage such that separation is easy as a butane gas after the reaction.

Tetrahydrofuran is used as a solvent in the above described reaction. Toluene and diethyl ether, and the like can also be used as other solvents, but the former has a possibility of slight progress of a side reaction and the latter has a possibility that a reaction intermediate is precipitated without being dissolved to decrease a reaction yield, and thus, tetrahydrofuran is preferable. The reaction can be carried out within the reaction temperature range from −78° C. to room temperature, and around 0° C. is suitable in consideration of suppression of a side reaction and efficiency.

A mixing ratio of each compound to be reacted cannot be clearly determined depending on compounds to be used, and generally, about 2 equivalent amount of nBuLi is added to a thioamide and then about 1 equivalent amount of a thioformamide is added thereto. The thioamide and nBuLi generate a dianion in a reaction with a ratio of 1:2, and the reaction progresses at almost 100% yield. Furthermore, since the generated dianion has high activity, a reaction at almost 100% with the thioformamide occurs. Therefore, a molar ratio of respective compounds is basically thioamide:nBuLi:thioformamide=1:2:1.

In the lower stage of the above described reactions, a thiazole skeleton is formed by a cyclization reaction in a molecule. In addition, due to a thioformamide used in this reaction, dihydrothiazole introduced with an amino group at the 5th position, which has never been known so far, is obtained. Both of carbon at the 5th position to which the amino group is bonded and carbon at the 4th position to which a phenyl group is bonded are asymmetric carbons, and can be used in various application developments including optical activity.

Addition of an organic magnesium compound (Grignard reagent), for example, PhMgBr and nBuMgBr, in a suitable amount in the reaction of the lower stage also makes it possible to promote a cyclization reaction.

By the way, 4,5-dihydro-1,3-thiazoles are materials that have been known before, and are particularly used as important intermediates for synthesis of active compounds based on dihydrothiazole and thiazole in the agricultural chemical and pharmaceutical industries (reference German patent No. DE10142749, etc.) In the present invention, since an amino group is introduced into the 5th position, the thiazole derivative is sufficiently expected as a raw material for new application development, in addition to the same applications of dihydrothiazole that has been used so far.

In the above described reaction process, a thioformamide is reacted and iodine is then further added thereto, thus a thiazole derivative represented by the general formula (V) can be obtained. As described above, when an aryl group is present at the 4th position (a phenyl group in the general formula (V)), dihydrothiazole is basically generated, but by adding iodine to the reaction system, it is considered to proceed de-protonation. Among thiazole derivatives thus obtained, at least one of $R^5$ and $R^6$ shown in the general formula (V) is an aryl group that may be substituted with one or more substituents selected from halogen, hydroxy, lower alkyl, lower alkoxy, and halo lower alkyl, or a heteroaromatic group that may be substituted with the same substituents, and thus, the derivative shows fluorescence emission.

[Formula 6]

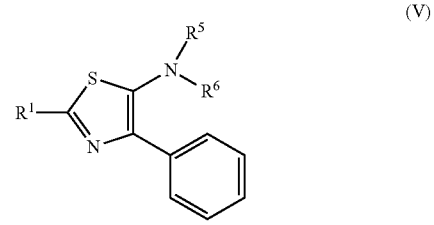

(V)

As reaction conditions at the time of iodine addition, a thioformamide is added at the above described reaction temperature (−78° C. to room temperature) and then reacted while mixing from about several minutes to several hours, thereafter adding iodine so as to have a molar concentration of an equivalent mole to 3 mole ratios, preferably 1.5 to 2.5 mole ratios with respect to the thioformamide, with keeping the reaction temperature. In addition of iodine, solid iodine can be directly added, or iodine can be once dissolved in a reaction solvent (e.g., tetrahydrofuran) and added to a reaction system. When iodine is reacted for about several minutes to several hours while stirring and the like after addition, a desired thiazole derivative represented by the general formula (V) having an aryl group at the 4th position can be obtained.

By the way, an EL element utilizing electroluminescence has characteristics such as having excellent impact resistance, since it has high visibility because of self-luminescence and is a complete solid-state element, and thus, such an EL element attracts attention for utilization as a light emitting element in various display devices. In particular, an organic EL element significantly reduces an applied voltage, and besides, it has characteristics such that miniaturization is easy and electric power consumption is small. Huge quantities of compound groups having a diarylamino group have been reported so far, and utilization as an organic EL element is now widely studied. A thiazole derivative represented by the above described general formula (V) has intensive fluorescence emission particularly when $R^5$ and $R^6$ are diarylamino groups. That is, a conjugated system of a diarylamino group extends even to a thiazole ring and a substituent phenyl, in this compound and, as a totally new electronic material, for example, a base compound that can be used for an electron transfer layer in an organic EL element can be created.

Next, a synthesis path of thiazole will be shown in the case of using a compound having a pyridyl group in $R^2$ as the above described amino group-containing compound:

[Formula 7]

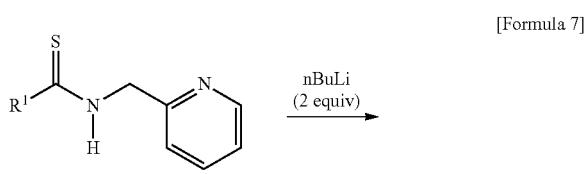

-continued

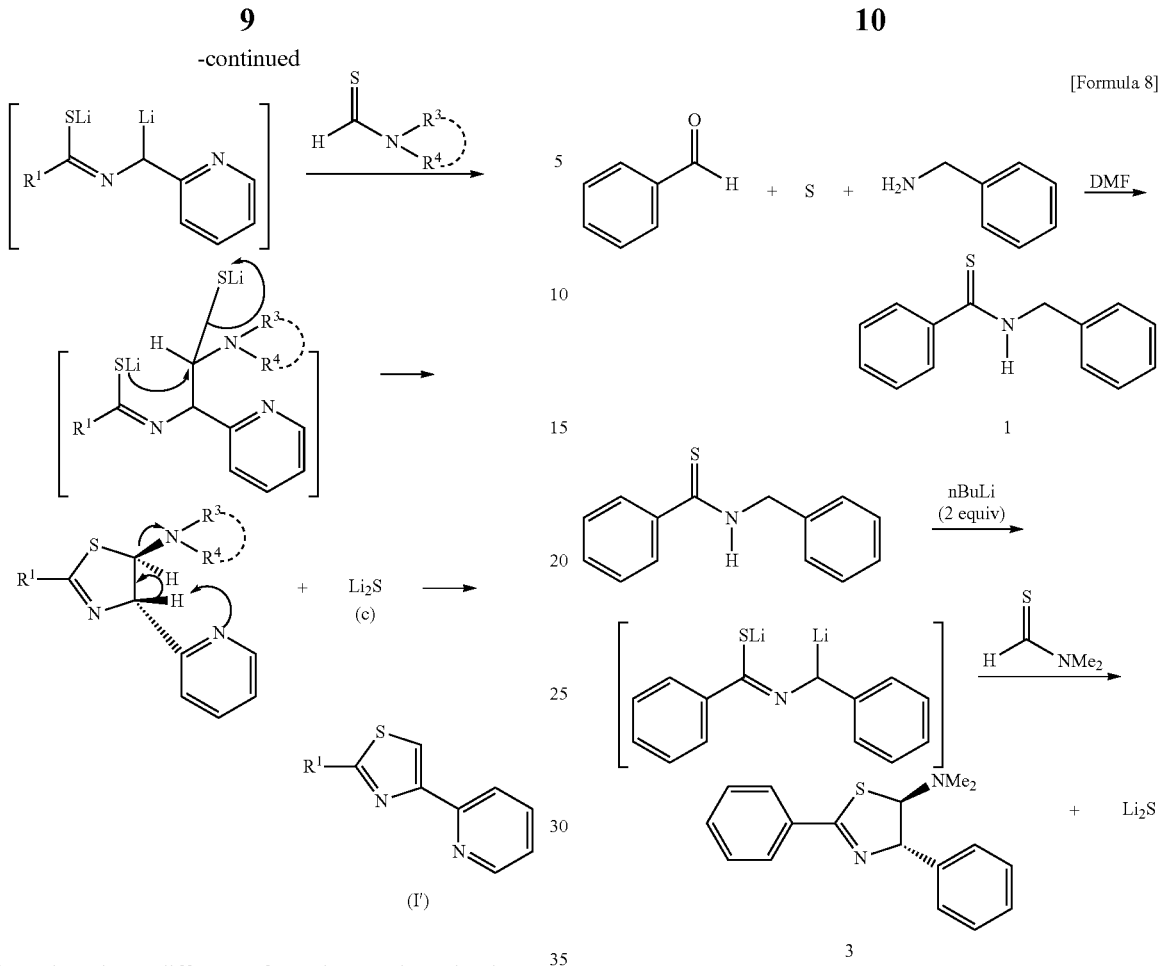

Since there is no difference from the reactions that have been already described until the upper and middle stages of the above described reactions, the lower stage will be only described herein. When nBuLi is acted on a thioamide having a pyridyl group to thus form a dianion, and a thioformamide is reacted thereto, although dihydrothiazole is once generated, de-protonation proceeds due to a nitrogen atom in a pyridyl group, and 4-(2-pyridyl)thiazole is generated by dehydrogenation. Such thiazole is useful as a functional compound (or a synthesis intermediate thereof) such as an agricultural chemical, a medical drug, a fungicide and a dye, and an electronic material, and in recent years, it is attracting attention also as a light emitting material for high-intensity brightness and colorization (particularly, realization of red light emission) of an organic EL.

An example using a thioamide bonded to the 2nd position of a pyridyl group was shown in the above described reaction formula (c), and a thioamide bonded to the 3rd or 4th position of a pyridyl group may be used. However, use of a thioamide bonded to the 2nd position of a pyridyl group is preferable since the final generated product (general formula (I')) can be obtained at the highest yield.

Some examples of the present invention will be shown below in order to more specifically clarify the present invention.

Example 1

The whole scheme for a synthesis method of compound 3 (4,5-dihydro-2,4-diphenyl-5-dimethylaminothiazole) is shown below as follows:

Synthesis of Compound 1
(N-phenylmethylbenzenecarbothioamide)

Benzaldehyde (10.1 mL, 0.1 mol) was added to a dimethyl formamide (DMF: 50 mL) solution of benzylamine (12.0 mL, 0.11 mol) at room temperature. Then, sulfur (3.52 g, 0.11 mol) was added thereto and heated while stirring at 80 to 90° C. for 6 hours. The reaction mixture solution was poured into ethyl ether (50 mL) and the organic layer was washed with an aqueous solution of saturated sodium hydrogen carbonate (200 mL) and hydrochloric acid (35%, 10 mL). Furthermore, the organic layer was dried with magnesium sulfate, filtrated and concentrated under reduced pressure, and the residue was re-crystallized with hexane/methylene chloride (1:1, 30 mL) to obtain 21.3 g (yield: 94%) of the compound 1 as a yellow solid.

Synthesis of Compound 3

The compound 1 (0.227 g, 1.0 mmol) was dissolved in THF (2.0 mL), and n-butyllithium-hexane solution (1.3 mL, 2.0 mmol) was gradually added to this solution at 0° C. After stirring for 5 minutes, N,N-dimethylthioformamide was added thereto at the same temperature and stirring was further continued for 2.5 hours. Water (10 mL) was added to the reaction mixture solution, and the organic layer was extracted with diethyl ether (10 mL). The organic layer was washed twice with water (10 mL), and an aqueous layer was further re-extracted with diethyl ether (5 mL). The organic layer collected was dried with magnesium sulfate, filtrated, and concentrated under reduced pressure, and the residue was purified by silica gel chromatography (developing solvent; Hexane:EtOAc:Et$_2$N=5:1:0.01) to obtain trans-4,5-dihydro-2,4-diphenyl-5-dimethylaminothiazole (0.14 g, 50%) as a light yellow solid.

Melting point at 89 to 91° C.

A H-nuclear magnetic resonance spectrum and a $^{13}$C-nuclear magnetic resonance spectrum of the compound 3 were measured, using JNMα-400 type manufactured by JEOL Ltd., at 25° C. in deuterated chloroform, and the $^1$H-nuclear magnetic resonance spectrum was measured 8 times of the number of integration, and the $^{13}$C-nuclear magnetic resonance spectrum was measured 100 to 200 times of the number of integration. Results thereof are shown as follows.

Trans-4,5-dihydro-2,4-diphenyl-5-dimethylaminothiazole $^1$H NMR (CDCl$_3$) δ2.11 (s, 6H, NMe$_2$), 5.11 (d, J=2.0 Hz, 1H, SCH), 5.6 (d, J=2.0 Hz, 1H, C=NCH), 7.08-7.19 (m, 5H, Ar), 7.27-7.35 (m, 3H, Ar), 7.90-7.92 (m, 2H, Ar); $^{13}$C NMR (CDCl$_3$) δ40.0 (NMe$_2$), 84.2 (SCH), 90.5 (C=NCH), 126.0, 127.6, 128.4, 128.5, 131.1, 133.5, 139.7, 168.7 (SCN)

IR data and MS data are also shown below together.

IR (KBr) 2947, 1597, 1450, 1355, 1265, 1229, 1051, 1027, 834, 754, 687, 651, 566, 521 cm$^{-1}$; MS (EI) m/z 282 (M$^+$); HRMS (EI) Calcd for C$_{17}$H$_{18}$N$_2$S (M$^+$) 282.1191. found: 282.1177.

Example 2

A mixing ratio, a temperature, a time and the like of each compound were the same operations as in Example 1, but "stirring was continued for 30 minutes and a phenyl magnesium bromide (PhMgBr) THF solution (1.09 M, 1.83 mL, 2.0 mmol) was added at room temperature and the mixture was stirred for 2 hours" instead of adding N,N-dimethylthioformamide at the same temperature and then continuing stirring for 2.5 hours. After that, operations were performed in the same manner as in Example 1 to obtain trans-4,5-dihydro-2,4-diphenyl-5-dimethylaminothiazole (0.235 g, 83%) as a light yellow solid. As shown in this example, addition of PhMgBr makes it possible to promote a cyclization reaction.

Example 3

Regarding a synthesis example of each of the dihydrothiazoles (3b to 3g) shown in Table 1 below, yields as well as the compound 1 and thioformamide which were used are shown in the same table. In addition, various conditions such as an amount to be used of each compound (molar ratio), a temperature, and a time are the same as in Example 2.

TABLE 1

| 1 (Thioamide) | Thioformamide | 3 (Thiazole derivative) | Yields |
|---|---|---|---|
| MeO-C$_6$H$_4$-C(=S)-NH-CH$_2$-Ph | H-C(=S)-NMe$_2$ | 3b: MeO-C$_6$H$_4$-thiazoline-NMe$_2$/Ph | 73% |
| (CH$_3$)$_2$CH-C(=S)-NH-CH$_2$-Ph | H-C(=S)-NMe$_2$ | 3c: iPr-thiazoline-NMe$_2$/Ph | 24% |
| 2-Py-C(=S)-NH-CH$_2$-Ph | H-C(=S)-NMe$_2$ | 3d: 2-Py-thiazoline-NMe$_2$/Ph | 19% |
| F-C$_6$H$_4$-C(=S)-NH-CH$_2$-Ph | H-C(=S)-NMe$_2$ | 3e: F-C$_6$H$_4$-thiazoline-NMe$_2$/Ph | 60% |
| (CH$_3$)$_3$C-C(=S)-NH-CH$_2$-Ph | H-C(=S)-NMe$_2$ | 3f: tBu-thiazoline-NMe$_2$/Ph | 36% |

TABLE 1-continued

| 1 (Thioamide) | Thioformamide | 3 (Thiazole derivative) | Yields |
|---|---|---|---|
| PhC(=S)NHCH2Ph | HC(=S)-morpholine | 3g (2-phenyl-5-morpholino-4-phenyl-4,5-dihydrothiazole) | 38% |

Measurement results such as a nuclear magnetic resonance spectrum for each dihydrothiazole shown in Table 1 are shown below.

Trans-4,5-dihydro-2-(4-methoxyphenyl)-4-phenyl-5-dimethylaminothiazole (3b); yellow oil IR (neat) 2951, 2833, 2786, 1605, 1508, 1254, 1170, 1031, 948, 837, 698, 657, 566 cm$^{-1}$; $^1$HNMR (CDCl$_3$) δ2.19 (s, 6H, NMe$_2$), 3.77 (s, 3H, OMe), 5.16 (d, J=2.0 Hz, 1H, SCH), 5.61 (d, J=2.0 Hz, 1H, C=NCH), 6.88-6.90 (d, J=8.8 Hz, 2H, Ar), 7.19-7.26 (m, 5H, Ar), 7.92-7.94 (m, 2H, Ar); $^{13}$C NMR (CDCl$_3$) δ40.0 (NMe$_2$), 55.2 (OMe), 84.2 (SCH), 90.4 (C=NCH), 113.6, 126.1, 126.2, 127.5, 128.5, 130.1, 140.0, 162.0, 168.0 (SCN); MS (EI) m/z 312 (M$^+$); HRMS (EI) Calcd for C$_{28}$H$_{20}$N$_2$OS (M$^+$) 312.1296. found: 312.1292.

Trans-2,4-dihydro-2-isopropyl-4-phenyl-5-dimethylaminothiazole (3c); yellow liquid IR (neat) 2966, 1614, 1454, 1287, 1044, 873, 835, 753, 699, 598 cm$^{-1}$; $^1$H NMR (CDCl$_3$) δ1.28 (dd, J=6.8 Hz, 2.0 Hz, 6H, CH(CH$_3$)$_2$), 2.13 (s, 6H, NMe$_2$), (sept, J=6.8 Hz, 1H, CH(CH$_3$)$_2$), 4.99 (d, J=2.0 Hz, 1H, SCH), 5.33-5.34 (d, J=2.0 Hz, 1H, C=NCH), 7.16-7.27 (m, 5H, Ar); $^{13}$C NMR (CDCl$_3$) δ21.6 (CH(CH$_3$)$_2$), 35.0 (CH(CH$_3$)$_2$), 40.0 (NMe$_2$), 83.5 (SCH), 89.7 (C=NCH), 126.0, 127.6, 128.6, 140.0, 178.6 (SCN); MS (EI) m/z 248 (M$^+$); HRMS (EI) Calcd for C$_{24}$H$_{20}$N$_2$S (M$^+$) 248.1347. found: 248.1354.

Trans-2,4-dihydro-2-(2-pyridyl)-4-phenyl-5-dimethylaminothiazole (3d); orange oil IR (neat) 3290, 3059, 2951, 2788, 1599, 1494, 1467, 1435, 1296, 1280, 1176, 1149, 1045, 1025, 996, 958, 836, 789, 743, 698, 537 cm$^{-1}$; $^1$H NMR (CDCl$_3$) δ2.11 (s, 6H, NMe$_2$), 5.14-5.15 (d, J=2.0 Hz, 1H, SCH), 5.63 (d, J=2.0 Hz, 1H, C=NCH), 7.18-7.22 (m, 2H, Ar), 7.24-7.25 (m, 2H, Ar), 7.30-7.37 (m, 2H, Ar) 7.68-7.73 (td, J=7.8 Hz, 2.0 Hz, 1H, Ar), 8.11-8.13 (d, J=8.29 Hz, 1H, Ar), 8.64-8.66 (d, J=8.29 Hz, 1H, Ar); $^{13}$C NMR (CDCl$_2$) δ40.1 (NMe$_2$), 84.9 (SCH), 88.9 (C=NCH), 121.9, 125.6, 126.2, 127.8, 128.7, 136.6, 139.6, 149.4, 151.3, 170.9 (SCN); MS (EI) m/z 283 (M$^+$); HRMS (EI) Calcd for C$_{26}$H$_{17}$N$_3$S (M$^+$) 283.1143. found: 283.1170.

Trans-4,5-dihydro-2-(4-fluorophenyl)-4-phenyl-5-dimethylaminothiazole (3e); orange oil IR (neat) 3062, 2949, 1603, 1506, 1451, 1234, 1154, 1028, 949, 842, 753, 698, 657, 562 cm$^{-1}$; $^1$H NMR (CDCl$_3$) δ2.20 (s, 6H, NMe$_2$), 5.22 (d, J=2.0 Hz, 1H, SCH), 5.63 (d, J=2.0 Hz, 1H, C=NCH), 7.05-7.10 (t, J=8.5 Hz, 2H, Ar), 7.23-7.31 (m, 5H, Ar), 7.95-8.00 (m, 2H, Ar); C NMR (CDCl$_2$) δ 40.1 (NMe$_2$), 84.3 (SCH), 91.1 (C=NCH), 126.0, 127.6, 128.4, 128.5, 131.1, 133.5, 139.7, 168.7 (SCN); F NMR (CDCl$_2$) δ −108.8; MS (EI) m/z 300 (M$^+$); HRMS (EI) Calcd for C$_{22}$H$_{17}$FN$_2$S (M$^+$) 300.1096. found: 300.1120.

Trans-2,4-dihydro-2-tertiary butyl-4-phenyl-5-dimethylaminothiazole (3f); yellow liquid IR (neat) 2965, 2360, 1611, 1451, 1362, 1042, 1002, 751, 698 cm$^{-1}$; $^1$H NMR (CDCl$_2$) δ1.39 (s, 9H, CH(CH$_3$)$_3$), 2.21 (s, 6H, NMe$_2$), 5.02-5.03 (d, J=1.5 Hz, 1H, SCH), 5.46-5.47 (d, J=1.5 Hz, 1H, C=NCH), 7.22-7.35 (m, 5H, Ar); C NMR (CDCl$_2$) δ29.6 (CH(CH$_3$)$_3$), 38.9 (CH(CH$_3$)$_3$), 40.0 (NMe$_2$), 83.8 (SCH), 89.5 (C=NCH), 125.9, 127.5, 128.5, 139.9, 181.5 (SCN); MS (EI) m/z 262 (M$^+$); HRMS (EI) Calcd for C$_{15}$H$_{22}$N$_2$S (M$^+$) 262.1504. found: 262.1500.

Trans-4,5-dihydro-2,4-diphenyl-5-morpholinothiazole (3g)

(m.p. 92-94° C.): IR (KBr) 2854, 1598, 1450, 1269, 1231, 1137, 1113, 945, 752, 565 cm$^{-1}$; $^1$H NMR (CDCl$_3$) δ 2.47-2.52 (m, 4H, N(CH$_2$)$_2$), 3.67-3.69 (m, 4H, O(CH$_2$)$_2$), 5.08-5.09 (d, J=2.0 Hz, 1H, SCH), 5.68 (d, J=2.0 Hz, 1H, C=NCH), 7.18-7.29 (m, 5H, Ar), 7.36-7.41 (m, 3H, Ar), 7.95-7.98 (m, 2H, Ar); $^{13}$C NMR (CDCl$_2$) δ47.9 (N(CH$_2$)$_2$), 66.3 (O(CH$_2$)$_2$), 83.6 (SCH), 89.1 (C=NCH), 126.2, 127.8, 128.5, 128.6, 128.7, 131.4, 133.3, 139.4, 168.8 (SCN); MS (EI) m/z 324 (M$^+$); HRMS (EI) Calcd for C$_{19}$H$_{20}$N$_2$OS (M$^+$) 324.1296. found: 324.1269.

Example 4

The whole scheme for a synthesis method of the compound 4 (2-phenyl-4-(2-pyridyl)thiazole) is shown below as follows:

[Formula 9]

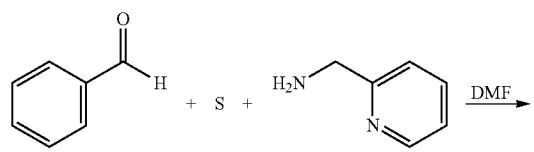

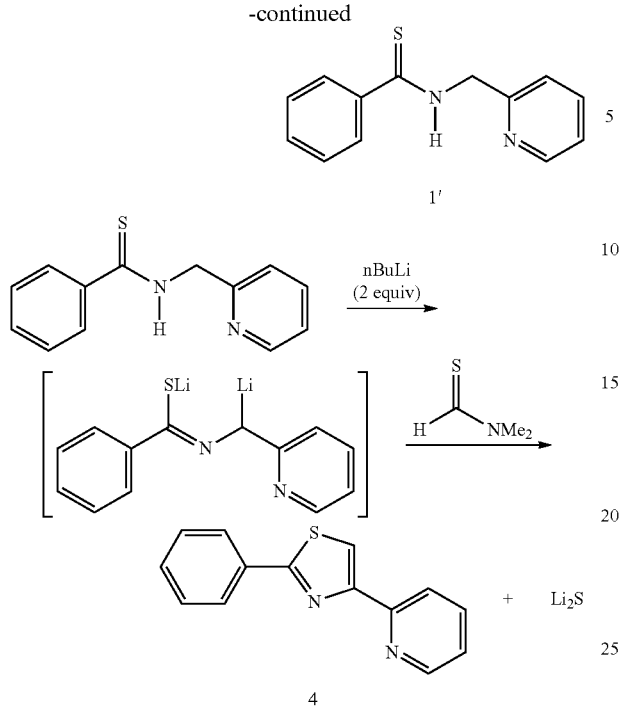

Synthesis of compound 1'
(N-(2-pyridylmethyl)benzenecarbothioamide)

Benzaldehyde (2.03 mL, 0.02 mol) was added to a dimethyl formamide (DMF: 8 mL) solution of pyridylmethylamine (2.22 mL, 0.022 mol) at room temperature. Sulfur (0.71 g, 0.022 mol) was then added thereto and the mixture was heated while stirring at 80 to 90° C. for 6 hours. The reaction mixture solution was poured into ethyl ether (20 mL), and the organic layer was washed with an aqueous solution of saturated sodium hydrogen carbonate (50 mL). Further, the organic layer was dried with magnesium sulfate, filtrated, and concentrated under reduced pressure, and the residue was purified by silica gel column chromatography (developing solvent; Hexane: EtOAc=2:1 to 1:2) to obtain 3.33 g (yield: 73%) of the compound 1 as a yellow solid.

Synthesis of Compound 4

The compound 1' (0.228 g, 1.0 mmol) was dissolved in THF (2.0 mL), and an n-butyllithium-hexane solution (1.3 mL, 2.0 mmol) was gradually added to this solution at 0° C. After stirring for 5 minutes, N,N-dimethylthioformamide was added thereto at the same temperature and stirring was further continued for 3 hours. Water (10 mL) was added to the reaction mixture solution, and the organic layer was extracted with diethyl ether (10 mL). The organic layer was washed twice with water (10 mL), and an aqueous layer was further re-extracted with diethyl ether (5 mL). The organic layer collected was dried with magnesium sulfate, filtrated, and concentrated under reduced pressure, and the residue was purified by silica gel chromatography (developing solvent; Hexane:EtOAc:Et$_2$N=5:1:0.01) to obtain 2-phenyl-4-(2-pyridyl)thiazole (0.149 g, 62%) as a light orange solid.

Melting point at 107 to 109° C.

The same various measurements were performed also on the obtained 2-phenyl-4-(2-pyridyl)thiazole, and results thereof are shown below.

IR (KBr) 2362, 1587, 1474, 1420, 1057, 991, 754, 684, 667, 591 cm$^{-1}$; $^1$H NMR (CDCl$_3$) δ 7.07-7.11 (m, 1H, Ar), 7.28-7.35 (m, 3H, Ar), 7.62-7.66 (td, J=7.6 Hz, 7.8 Hz, 1H, Ar), 7.91-7.93 (m, 2H, Ar), 7.97 (s, 1H, SCH), 8.14-8.16 (d, J=7.8 Hz, 1H, Ar), 8.50-8.51 (d, J=3.9 Hz, 1H, Ar); $^{13}$C NMR (CDCl$_3$) δ116.8, 121.2, 122.7, 126.5, 128.8, 130.0, 133.5, 136.8, 149.3, 152.5, 156.0, 167.9 (SCN); MS (EI) m/z 238 (M$^+$); HRMS (EI) Calcd for C$_{14}$H$_{10}$N$_2$S (M$^+$) 238.0565. found: 238.0572.

Example 5

Regarding a synthesis example of each of the pyridyl thiazoles (4b to 4h) shown in Table 2 below, yields as well as the compound 1 that was used are shown in the same table. In addition, various conditions such as an amount to be used of each compound (molar ratio), a temperature, and a time are the same as in Example 4.

TABLE 2

| 1' (Thioamide) | 4 (Thiazole derivative) | Yields |
|---|---|---|
|  | 4b | 46% |
|  | 4c | 38% |

TABLE 2-continued

| 1' (Thioamide) | 4 (Thiazole derivative) | Yields |
|---|---|---|
| 4-MeO-C6H4-C(=S)-NH-CH2-(2-pyridyl) | 2-(4-MeO-C6H4)-4-(2-pyridyl)thiazole (4d) | 85% |
| 4-F-C6H4-C(=S)-NH-CH2-(2-pyridyl) | 2-(4-F-C6H4)-4-(2-pyridyl)thiazole (4e) | 46% |
| 4-CF3-C6H4-C(=S)-NH-CH2-(2-pyridyl) | 2-(4-CF3-C6H4)-4-(2-pyridyl)thiazole (4f) | 37% |
| iPr-C(=S)-NH-CH2-(2-pyridyl) | 2-iPr-4-(2-pyridyl)thiazole (4g) | 64% |
| tBu-C(=S)-NH-CH2-(2-pyridyl) | 2-tBu-4-(2-pyridyl)thiazole (4h) | 24% |

Measurement results such as a nuclear magnetic resonance spectrum for each pyridyl thiazole shown in Table 2 are shown below.

2,4-di(2-pyridyl)thiazole (4b)

$^1$H NMR (CDCl$_3$) δ7.12-7.16 (m, 1H, Ar), 7.20-7.24 (m, 1H, Ar), 7.67-7.72 (m, 2H, Ar), 8.11-8.16 (m, 2H, Ar), 8.20-8.22 (d, J=7.8 Hz, 1H, Ar), 8.52-8.55 (m, 2H, Ar).

2-thiophen-4-(2-pyridyl)thiazole (4c)

(m.p. 114-115° C.): IR (KBr) 3126, 1587, 1473, 1424, 1227, 1052, 830, 767, 698 cm$^{-1}$; $^1$H NMR (CDCl$_3$) δ7.09-7.10 (m, 1H, Ar), 7.22-7.25 (m, 1H, Ar), 7.42-7.43 (dd, J=4.9 Hz, 1.0 Hz, 1H, Ar), 7.56-7.58 (dd, J=3.9 Hz, 1.0 Hz, 1H, Ar), 7.76-7.80 (m, 1H, Ar), 8.04 (s, 1H, SCH), 8.23-8.25 (d, J=7.8 Hz, 1H), 8.63-8.64 (m, 1H, Ar); $^{13}$C NMR (CDCl$_3$) δ116.0, 121.3, 122.8, 126.6, 127.6, 127.7, 136.8, 137.2, 149.3, 152.2, 155.6, 161.5 (SCN); MS (EI) m/z 244 (M$^+$); HRMS (EI) Calcd for C$_{12}$H$_8$N$_2$S$_2$ (M$^+$) 244.0129. found: 244.0105.

2-(4-methoxyphenyl)-4-(2-pyridyl)thiazole (4d)

(m.p. 100-103° C.): IR (KBr) 3085, 2836, 1605, 1476, 1306, 1247, 1180, 1026, 834, 776, 713 cm$^{-1}$; $^1$H NMR (CDCl$_3$) δ3.76 (s, 1H, OMe), 6.85-6.89 (d, J=8.8 Hz, 2H, Ar), 7.11-7.17 (m, 1H, Ar), 7.66-7.70 (td, J=7.8 Hz, 2.0 Hz, 1H, Ar), 7.86-7.90 (d, J=8.8 Hz, 2H, Ar), 7.93 (s, 1H, SCH), 8.15-8.17 (d, J=7.8 Hz, 1H, Ar), 8.52-8.54 (m, 1H, Ar); $^{13}$C NMR (CDCl$_3$) δ55.3 (CH$_3$), 114.2, 116.0, 121.2, 122.7, 126.5, 128.0, 136.9, 149.3, 152.6, 155.7, 161.1, 167.9 (SCN); MS (EI) m/z 268 (M$^+$); HRMS (EI) Calcd for C$_{15}$H$_{12}$N$_2$OS (M$^+$) 268.0670. found: 268.0663.

2-(4-fluorophenyl)-4-(2-pyridyl)thiazole (4e)

(m.p. 140-144° C.): IR (KBr) 3103, 1588, 1519, 1477, 1229, 1060, 994, 832, 751, 581, 505 cm$^{-1}$; $^1$H NMR (CDCl$_3$)

δ 7.12-7.18 (t, J=8.8 Hz, 2H, Ar), 7.22-7.25 (m, 1H, Ar), 7.76-7.81 (td, J=7.82 Hz, 1H, Ar), 7.99-8.04 (m, 2H, Ar), 8.08 (s, 1H, SCH), 8.23-8.25 (d, J=7.81 Hz, 1H, Ar), 8.63-8.64 (m, 1H, Ar); $^{13}$C NMR (CDCl$_3$) δ115.8, 116.0, 116.8, 121.2, 122.8, 129.9, 129.9, 136.9, 149.3, 152.4, 156.0, 162.6 165.1, 166.8 (SCN); $^{19}$F NMR (CDCl$_3$) δ −20.0; MS (EI) m/z 256 (M$^+$); HRMS (EI) Calcd for C$_{14}$H$_9$FN$_2$S (M$^+$) 256.0470. found: 256.0474.

2-(4-trifluoromethylphenyl)-4-(2-pyridyl)thiazole (4f)

(m.p. 123-127° C.): IR (KBr) 2361, 1588, 1475, 1407, 1327, 1162, 1110, 1068, 846, 764, 673, 608 cm$^{-1}$; $^1$H NMR (CDCl$_3$) δ7.13-7.17 (m, 1H, Ar), 7.59-7.91 (d, J=8.3 Hz, 2H, Ar), 7.66-7.71 (td, J=7.6 Hz, 1H, Ar), 8.01-8.03 (m, 3H, Ar), 8.13-8.15 (d, J=7.8 Hz, 1H, Ar), 8.52-8.54 (d, J=4.9 Hz, 1H, Ar); $^{13}$C NMR (CDCl$_3$) δ117.8, 121.3, 122.5, 123.0, 125.8, 125.9, 126.7, 131.4, 131.7, 136.6, 136.9, 149.4, 152.2, 156.6, 166.0 (SCN); $^{19}$F NMR (CDCl$_3$) δ −63.1; MS (EI) m/z 306 (M$^+$); HRMS (EI) Calcd for C$_{15}$H$_9$F$_3$N$_2$S (M$^+$) 306.0439. found: 306.0428.

2-isopropyl-4-(2-pyridyl)thiazole (4g)

Orange liquid: IR (neat) 2967, 1588, 1496, 1420, 1331, 1051, 754, 621 cm$^{-1}$; $^1$H NMR (CDCl$_3$) δ1.35-1.37 (d, J=7.3 Hz, 6H, CH(C$\underline{H}_3$)$_2$), 3.25-3.35 (sept, J=6.9 Hz, 1H, C$\underline{H}$(CH$_3$)$_2$), 7.08-7.11 (m, 1H, Ar), 7.62-7.67 (td, J=7.6 Hz, 1H, Ar), 7.84 (s, 1H, SCH), 8.02-8.04 (d, J=7.84 Hz, 1H, Ar), 8.51-8.52 (d, J=4.9 Hz, 1H, Ar) $^{13}$C NMR (CDCl$_3$) δ23.1 (CH(C$\underline{H}_3$)$_2$), 33.4 (C$\underline{H}$(CH$_3$)$_2$), 115.6, 121.1, 122.4, 136.8, 149.3, 152.8, 154.5, 178.0 (SCN); MS (EI) m/z 204 (M$^+$); HRMS (EI) Calcd for C$_{11}$H$_{12}$N$_2$S (M$^+$) 204.0721. found: 204.0691.

2-tertiary butyl-4-(2-pyridyl)thiazole (4h)

Orange oil: IR (neat) 2961, 2925, 1588, 1495, 1463, 1065, 994, 754 cm$^{-1}$; $^1$H NMR (CDCl$_3$) δ1.42 (s, 9H, C(CH$_3$)$_3$), 7.10-7.19 (m, 1H, Ar), 7.65-7.69 (td, J=7.8 Hz, 1H, Ar), 7.85 (s, 1H, SCH), 8.08-8.10 (dd, J=7.8 Hz, 1.0 Hz, 1H, Ar), 8.51-8.52 (d, J=7.8 Hz, 1H, Ar); $^{13}$C NMR (CDCl$_3$) δ30.9 (C(C$\underline{H}_3$)$_3$), 37.8 (C(CH$_3$)$_3$), 115.6, 121.3, 122.4, 136.8, 149.3, 153.0, 154.4, 181.1 (SCN); MS (EI) m/z 218 (M$^+$); HRMS (EI) Calcd for C$_{12}$H$_{14}$N$_2$S (M$^+$) 218.0878. found: 218.0857.

Example 6

The whole scheme for a synthesis method of the compound 5 (2-(4-methoxyphenyl)-4-phenyl-5-diphenylaminothiazole) by a reaction of adding iodine is then shown as follows:

Specifically, the compound 1 shown in Example 1 was synthesized, the compound 1 (0.257 g, 1.0 mmol) was then dissolved in THF (2.0 mL), a BuLihexane solution (1.43 M, 1.40 mL, 2.0 mmol) was added to this solution at 0° C., and the mixture was stirred for 5 minutes. N,N-diphenylthioformamide (0.213 g, 1.0 mmol) was added to the solution at 0° C., and the mixture was stirred for 30 minutes. Thereto was added iodine (0.512 g, 2.0 mmol) at 0° C., and stirring was continued for 2 hours. The reaction mixture solution was poured into a saturated solution of ammonium chloride and extracted with methylene chloride. The organic layer was dried with magnesium sulfate and concentrated. The residue was purified by silica gel column chromatography to obtain 2-(4-methoxyphenyl)-4-phenyl-5-diphenylaminothiazole at a yield of 26% as a yellow solid.

Measurement results such as a nuclear magnetic resonance spectrum for the compound 5 are shown below. A fluorescence spectrum (solid line) by a fluorescence spectrometer of the compound is shown in FIG. 1. A fluorescent intensity is a value when that of rhodamine B was assumed to be 100 in the FIGURE. In this FIGURE, a fluorescence spectrum (dashed line) of 2-(4-methoxyphenyl)-4-phenyl-5-dimethylaminothiazole is shown for comparison, and an effect in the case where a diphenylamino group was used as a substituent is prominently shown.

2-(4-methoxyphenyl)-4-phenyl-5-diphenylaminothiazole mp.: 152-155° C.; IR (KBr) 3064, 2926, 2839, 1602, 1515, 1490, 1415, 1341, 1290, 1245, 1173, 1029, 975, 838, 748, 514 cm$^{-1}$; $^1$H NMR (CDCl$_3$) δ3.75 (s, 3H, OMe), 6.86 (d, J=8.8 Hz, 2H, Ar), 6.90 (t, J=7.3 Hz, 2H, Ar), 7.05-7.07 (m, 4H, Ar), 7.10-7.20 (m, 7H, Ar), 7.82 (d, J=8.8 Hz, 2H, Ar), 7.85-7.88 (m, 2H, Ar); $^{13}$C NMR (CDCl$_3$) δ55.4 (OMe), 114.1, 121.3, 122.9, 127.0, 127.4, 127.7, 127.9, 128.2, 129.2, 133.4, 138.9, 146.5, 148.6, 161.2, 163.6 (SC=N); MS (EI) m/z 434 (M$^+$); HRMS (EI) Calcd for C$_{28}$H$_{22}$N$_2$OS (M$^+$) 434.1453. found: 434.1437.

Example 7

The same operations were performed except for using N-phenyl-N-methylthioformamide (0.119 g, 1.0 mmol) in place of N,N-diphenylthioformamide in Example 6, to obtain 2-(4-methoxyphenyl)-4-phenyl-5-(N-phenyl-N-methylamino) thiazole at a yield of 19% as a yellow solid.

2-(4-methoxyphenyl)-4-phenyl-5-(N-phenyl-N-methylamino) thiazole mp.: 100-101° C.; IR (KBr) 2939, 1904, 1596, 1491, 1298, 1258, 1221, 1168, 1136, 1111, 1028, 977, 833, 751, 701

[Formula 10]

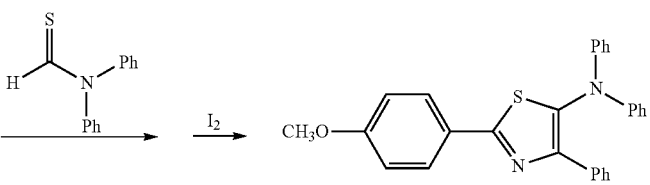

cm$^{-1}$; $^1$H NMR (CDCl$_3$) δ3.10 (s, 3H, NMe), 3.74 (s, 3H, OMe), 6.76-6.87 (m, 5H, Ar), 7.12-7.21 (m, 3H, Ar), 7.26 (t, J=7.3 Hz, 2H, Ar), 7.83 (d, J=9.4 Hz, 2H, Ar), 7.90 (d, J=7.32 Hz, 2H, Ar); $^{13}$C NMR (CDCl$_3$) δ40.3 (NMe), 55.3 (OMe), 114.1, 114.2, 119.3, 127.1, 127.3, 127.7, 127.9, 128.5, 129.1, 133.8, 141.0, 148.3, 148.4, 161.1, 163.2 (SC=N); MS (EI) m/z 372 (M$^+$).

INDUSTRIAL APPLICABILITY

The thiazole derivative of the present invention can be simply produced from easily available raw materials without undergoing a complicated synthesis path by the production process of the present invention. For a synthesized product, specifying a substituent of a starting substance makes it possible to obtain a generated product selectively, and also, a totally novel compound that has never existed so far can be easily obtained. Therefore, the obtained thiazole derivative can be utilized as a material (and an intermediate) of a novel compound useful as medical drugs and agricultural chemicals, etc.

The invention claimed is:

1. A process for producing a thiazole derivative, comprising:
    dissolving a secondary N-arylmethyl thioamide or secondary N-pyridylmethyl thioamide in a solvent;
    adding a strong base to the solution with mixing, while maintaining said solution between −78° C. and ambient temperature,
        wherein the strong base is selected from the group consisting of n-butyllithium, lithium, diisopropylamide, sodium hydride, potassium hydride, potassium t-butoxide, calcium hydride, sodium hydroxide, and sodium amide;
    adding a thioformamide selected from the group consisting of N,N-dimethylthioformamide, N-morpholinothioformamide, and N,N-diphenylthioformamide to form the thiazole derivative; and
    adding a thioformamide to form the thiazole derivative.

2. The process of claim 1, wherein the secondary N-arylmethyl thioamide is N-phenylmethylbenzenecarbothioamide (1), the thioformamide is N,N-dimethylthioformamide, and the thiazole derivative is trans-4,5-dihydro-2,4-diphenyl-5-dimethylaminothiazole (3), or the secondary N-pyridylmethylthioamide is N-(2-pyridylmethyl)benzenecarbothioamide (1'), the thioformamide is N,N-dimethylthioformamide, and the thiazole derivative is 2-phenyl-4-(2-pyridyl)thiazole (4).

3. The process of claim 1, wherein the secondary N-arylmethyl thioamide, the thioformamide, and the thiazole derivative are selected from the groups consisting of
    the secondary N-arylmethyl thioamide is N-benzyl-4 methoxybenzenecarbothioamide, the thioformamide is N,N-dimethylthioformamide, and the thiazole derivative is trans-4,5-dihydro-2-(4-methoxyphenyl)-4-phenyl-5-dimethylaminothiazoline (3b),
    the secondary N-arylmethyl thioamide is N-benzylisopropylbenzenecarbothioamide, the thioformamide is N,N-dimethylthioformamide, and the thiazole derivative is trans-4,5-dihydro-2-isopropyl-4-phenyl-5-dimethylaminothiazoline (3c),
    the secondary N-arylmethyl thioamide is N-benzyl-2-pyridylcarbothioamide, the thioformamide is N,N-dimethylthioformamide, and the thiazole derivative is trans-4,5-dihydro-2-(2-pyridyl)-4-phenyl-5-dimethylaminothiazoline (3d),
    the secondary N-arylmethyl thioamide is N-benzyl-4 fluorobenzenecarbothioamide, the thioformamide is N,N-dimethylthioformamide, and the thiazole derivative is trans-4,5-dihydro-2-(4-fluorophenyl)-4-phenyl-5-dimethylaminothiazoline (3e),
    the secondary N-arylmethyl thioamide is N-benzyl-t-butylcarbothioamide, the thioformamide is N,N-dimethylthioformamide, and the thiazole derivative is trans-4,5-dihydro-2-t-butyl-4-phenyl-5-dimethylaminothiazoline (3f), and
    the secondary N-arylmethyl thioamide is N-benzylbenzenecarbothioamide, the thioformamide is N-morpholinothioformamide, and the thiazole derivative is trans-4,5-dihydro-2,4-diphenyl-5-morpholinothiazoline (3g).

4. The process of claim 1, wherein the secondary N-pyridylmethyl thioamide, the thioformamide, and the thiazole derivative are selected from the groups consisting of
    the secondary N-pyridylmethylthioamide is N-(2-picolylamine)-2-pyridinecarbothioamide, the thioformamide is N,N-dimethylthioformamide, and the thiazole derivative is 2,4-di(2-pyridyl) thiazole (4b),
    the secondary N-pyridylmethylthioamide is N-(2-picolylamine)-2-thiophenecarbothioamide, the thioformamide is N,N-dimethylthioformamide, and the thiazole derivative is 2-thiophen-4-(2-pyridyl)thiazole (4c),
    the secondary N-pyridylmethylthioamide is N-(2-pyridinylmethan)-4-methoxy-1-phenylcarbothioamide, the thioformamide is N,N-dimethylthioformamide, and the thiazole derivative is 2-(4-methoxyphenyl)-4-(2-pyridyl)thiazole (4d),
    the secondary N-pyridylmethylthioamide is N-(2-pyridinylmethan)-4-fluoro-1-phenylcarbothioamide, the thioformamide is N,N-dimethylthioformamide, and the thiazole derivative is 2-(4-fluorophenyl)-4-(2-pyridyl)thiazole (4e), the secondary N-pyridylmethylthioamide is N-(2-pyridinylmethan)-4-trifluoromethyl-1-phenylcarbothioamide, the thioformamide is N,N-dimethylthioformamide, and the thiazole derivative is 2-(4-trifluoromethylphenyl)-4-(2-pyridyl)thiazole (4f),
    the secondary N-pyridylmethylthioamide is N-(2-picolylamine)isopropylcarbothioamide, the thioformamide is N,N-dimethylthioformamide, and the thiazole derivative is 2-isopropyl-4-(2-pyridyl)thiazole (4g), and
    the secondary N-pyridylmethylthioamide is N-(2-picolylamine)-t-butylcarbothioamide, the thioformamide is N,N-dimethylthioformamide, and the thiazole derivative is 2-isopropyl-4-(2-pyridyl)thiazole (4h).

5. The method of claim 1, comprising:
    adding iodine when the thioamide is a secondary N-arylmethyl thioamide.

6. The process of claim 5, wherein the secondary N-arylmethyl thioamide is N-phenylmethylbenzenecarbothioamide (1), the thioformamide is N,N-dimethylthioformamide, and the thiazole derivative is 2,4-diphenyl-5-dimethylaminothiazole.

7. The process of claim 5, wherein the secondary N-arylmethyl thioamide, the thioformamide, and the thiazole derivative are selected from the groups consisting of
    the secondary N-arylmethyl thioamide is N-benzyl-4-methoxybenzenecarbothioamide, the thioformamide is N,N-dimethylthioformamide, and the thiazole derivative is 2-(4-methoxyphenyl)-4-phenyl-5-dimethylaminothiazole,
    the secondary N-arylmethyl thioamide is N-benzylisopropylcarbothioamide, the thioformamide is N,N-dimethylthioformamide, and the thiazole derivative is 2-isopropyl-4-phenyl-5-dimethylaminothiazole,
    the secondary N-arylmethyl thioamide is N-benzyl-2-pyridinecarbothioamide, the thioformamide is N,N-dimethylthioformamide, and the thiazole derivative is 2-isopropyl-4-phenyl-5-dimethylaminothiazole, the secondary N-arylmethyl thioamide is N-benzyl-4-fluorobenzenecarbothioamide, the thioformamide is N,N-dimethylthioformamide, and the thiazole derivative is 2-(4-fluorophenyl)-4-phenyl-5-dimethylaminothiazole, the secondary N-arylmethyl thioamide is N-benzyl-t-butylcarbothioamide, the thioformamide is N,N-dimethylthioformamide, and the thiazole derivative is 2-t-butyl-4-phenyl-5-dimethylaminothiazole, the secondary N-arylmethyl thioamide is N-benzylbenzenecarbothioamide, the thioformamide is N-morpholinothioformamide, and the thiazole derivative is 2,4-diphenyl-5-morpholinothiazole (3g), the secondary N-arylmethyl thioamide is N-benzyl-4-methoxybenzenecarbothioamide, the thioformamide is N,N-diphenylthioformamide, and the thiazole derivative is 2-(4-methoxyphenyl)-4-phenyl-5-diphenylaminothiazole (5), and the secondary N-arylmethyl thioamide is N-benzyl-4-methoxybenzenecarbothioamide, the thioformamide is N-phenyl-N-methylthioformamide, and the thiazole derivative is (2-(4-methoxyphenyl)-4-phenyl-5-(N-phenyl-N-methylamino) thiazole).

* * * * *